United States Patent [19]

Chasar

[11] Patent Number: 4,507,416

[45] Date of Patent: Mar. 26, 1985

[54] 2,4,6-TRIS(SUBSTITUTED PHENOXY)-1,3,5,2,4,6-TRIOXATRIPHOSPHORINANES AS STABILIZERS

[75] Inventor: Dwight W. Chasar, Northfield, Ohio

[73] Assignee: The B. F. Goodrich Company, Akron, Ohio

[21] Appl. No.: 493,894

[22] Filed: May 12, 1983

[51] Int. Cl.$^3$ ............................. C08K 5/52; C07F 9/15
[52] U.S. Cl. ................................. 524/101; 260/927 R; 260/988; 524/117; 252/400 R
[58] Field of Search ................... 260/927 R, 933, 988; 524/101, 117; 252/400.24

[56] References Cited

U.S. PATENT DOCUMENTS 4,025,486 5/1977 Gilles ............................... 260/927 R Primary Examiner—Anton H. Sutto
Attorney, Agent, or Firm—J. Hughes Powell, Jr.; Alan A. Csontos

[57] ABSTRACT

Novel stabilizers for organic materials subject to degradation, 2,4,6-tris(substituted phenoxy)-1,3,5,2,4,6-trioxatriphosphorinanes are prepared by the reaction of substituted-phenylphosphorodichloridites, water and amines. The 2,4,6-tris(substituted phenoxy)-1,3,5,2,4,6-trioxatriphosphorinanes, form effective stabilizer combinations with hindered and partly hindered phenols such as hydroxyphenylalkyleneyl isocyanurates, particularly when used in polymers, polyolefins, for example.

23 Claims, No Drawings

2,4,6-TRIS(SUBSTITUTED PHENOXY)-1,3,5,2,4,6-TRIOXATRIPHOSPHORINANES AS STABILIZERS

BACKGROUND OF THE INVENTION

Extensive research has been directed to the preparation and evaluation of organic phosphite compounds as stabilizers. A number of aromatic phosphorus containing stabilizers for polymers are known. Some of these are effective against heat degradation of polymers and some of them find use in combination with other stabilizers for the same or different functions. While some of these have been made available commercially, many of them have limited application because of deficiencies that limit their general application. Many of these phosphorus containing materials are expensive and they have varying degrees of effectiveness when combined with other stabilizers. Further, some of the most effective materials have some deficiencies such as lack of hydrolytic stability and the like. New phosphite compounds that are effective anti-oxidants, are readily and inexpensively prepared, and that particularly exhibit enhanced polymer protection against heat and oxygen when combined with hydroxyphenyl isocyanurate compounds and other hindered or partly hindered phenol compounds are desired.

SUMMARY OF THE INVENTION

Novel stabilizers for organic materials subject to degradation, 2,4,6-tris(substituted phenoxy)-1,3,5,2,4,6-trioxatriphosphorinanes, prepared by the reaction of substituted-phenylphosphorodichloridites, water and amines, form particularly effective stabilizer combinations with hindered phenol compounds, particularly hydroxyphenylalkyleneyl isocyanurates.

DETAILED DESCRIPTION

The 2,4,6-tris(substituted phenoxy)-1,3,5,2,4,6-trioxatriphosphorinanes may be represented by the structural formulas (1)

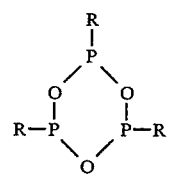

wherein

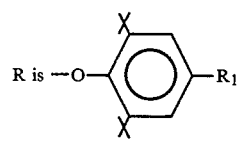

or

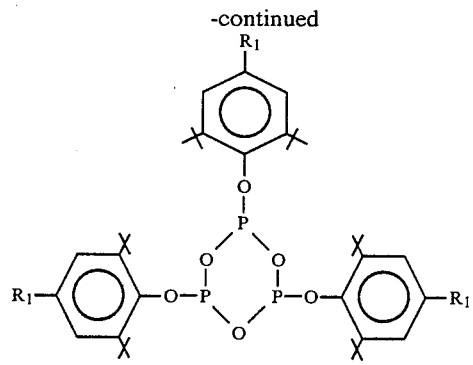

wherein + is t-butyl or t-pentyl and $R_1$ is hydrogen, primary, secondary, and tertiary alkyl radicals containing 1 to 9 carbon atoms such as methyl, ethyl, isopropyl, n-butyl, t-butyl, amyl, t-amyl, hexyl; heptyl, 2-methyl hexyl, 2-ethyl hexyl, octyl, isooctyl, and the like, cycloalkyl radicals containing 3 to 6 carbon atoms, halogen, $C{\equiv}N$, alkoxy radicals containing 1 to 8 carbon atoms, such as methoxy, ethoxy, butoxy and the like, phenyl, $COOR_2$ wherein $R_2$ is an alkyl radical containing 1 to 8 carbon atoms, $-CH_2CH_2COOR_3$ wherein $R_3$ is an alkyl radical containing 1 to 18 carbon atoms, and $-C(CH_3)_2CON(R_4)_2$ wherein $R_4$ is an alkyl group of 1 to 9 carbon atoms.

Preferably + is t-butyl and $R_1$ is hydrogen, an alkyl radical containing 1 to 4 carbon atoms, alkoxy radicals containing 1 to 4 carbon atoms, $-COOR_2$, $-CH_2CH_2COOR_3$, and $-C(CH_3)_2CON(R_4)_2$ radical wherein $R_3$ is an alkyl radical containing 1 to 4 carbon atoms, $R_2$ is an alkyl radical containing 1 to 4 carbon atoms and $R_4$ is an alkyl radical containing 1 to 4 carbon atoms.

Typical 2,4,6-tris(substituted phenoxy)-1,3,5,2,4,6-trioxatriphosphorinanes are 2,4,6-tris(2,6-di-t-butylphenoxy)-1,3,5,2,4,6-trioxatriphosphorinanes and 2,4,6-tris(2,6-di-t-butyl-4-substituted phenoxy)-1,3,5,2,4,6-trioxatriphosphorinanes wherein the radicals substituted at the 4-position are those described above. Typical compounds are 2,4,6-tris(2,6-di-t-butyl-4-methylphenoxy)-1,3,5,2,4,6-trioxatriphosphorinane, 2,4,6-tris(2,6-di-t-butyl-4-ethylphenoxy)-1,3,5,2,4,6-trioxatriphosphorinane, 2,4,6-tris(2,6-di-t-butyl-4-propylphenoxy)-1,3,5,2,4,6-trioxatriphosphorinane, 2,4,6-tris(2,6-di-t-butyl-4-isopropylphenoxy)-1,3,5,2,4,6-trioxatriphosphorinane, 2,4,6-tris(2,6,-di-t-butyl-4-n-butylphenoxy)-1,3,5,2,4,6-trioxatriphosphorinane, 2,4,6-tris(2,6-di-t-butyl-4-isoamylphenoxy)-1,3,5,2,4,6-trioxatriphosphorinane, 2,4,6-tris(2,6-di-t-butyl-4-methoxyphenoxy)-1,3,5,2,4,6-trioxatriphosphorinane, 2,4,6-tris(2,6-di-t-butyl-4-ethoxyphenoxy)-1,3,5,2,4,6-trioxatriphosphorinane, 2,4,6-tris(2,6-di-t-butyl-4-carbomethoxyphenoxy)-1,3,5,2,4,6-trioxatriphosphorinane, 2,4,6-tris(2,4,6-tri-t-butylphenoxy)-1,3,5,2,4,6-trioxatriphosphorinane, 2,4,6-tris[2,6-di-t-butyl-4-(2-carboethoxyethyl)phenoxy]-1,3,5,2,4,6-trioxatriphosphorinane, 2,4,6-tris[2,6-di-t-butyl-4-(1-methyl-1-diethylcarbamoylethyl)phenoxy]-1,3,5,2,4,6-trioxatriphosphorinane, and 2,4,6-tris[2,6-di-t-butyl-4-(2-carbooctadecyloxyethyl)phenoxy]-1,3,5,2,4,6-trioxatriphosphorinane.

The method to make the 2,4,6-tris(substituted phenoxy)-1,3,5,2,4,6-trioxatriphosphorinanes, while uncomplex, is novel. A substituted phenylphosphorodichloridite is reacted with water and an amine in a non-protic solvent at low temperatures for short periods of time and the resulting 2,4,6-tris(substituted phenoxy)-1,3,5,2,4,6-trioxatriphosphorinane is obtained by filtering the reaction mixture, evaporating the filtrate and washing the crude product.

Substituted phenylphosphorodichloridites used in the process of the invention include those substituted at the 2,6- and 2,4,6-positions on the phenyl group. The 2- and 6-positions are substituted with the t-butyl groups, while the 4-position may be substituted with the alkyl, alkoxy, carboxyester, and like radicals as set forth for the

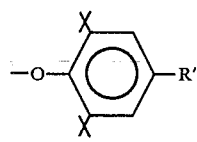

radical above.

Typical reactants include 2,6-di-t-butyl-4-methylphenylphosphorodichloridite, 2,6-di-t-butyl-4-ethylphenylphosphorodichloridite, 2,6-di-t-butyl-4-propylphenylphosphorodichloridite, 2,6-di-t-butyl-4-n-butylphenylphosphorodichloridite, 2,6-di-t-butyl-4-t-butylphenylphosphorodichloridite, 2,6-di-t-butyl-4-methoxyphenylphosphorodichloridite, 2,6-di-t-butyl-4-ethoxyphenylphosphorodichloridite, 2,6-di-t-butyl-4-carbomethoxyphenylphosphorodichoridite, 2,6-di-t-butyl-phenylphosphorodichlororidite, 2,6-di-t-butyl-4-(1-methyl-1-diethylcarbamoylethyl)phenylphosphorodichloridite and 2,6-di-t-butyl-4-(2-carboethoxyethyl)-phenylphosphorodichloridite and the like.

The amine may be any amine, but more preferably is an alkylamine such as trialkylamines including trimethylamine, triethylamine, tripropylamine, wherein the alkyl radicals contain 1 to 8 carbon atoms, pyridine, N,N-dimethylaniline, and the like.

The solvents are organic non-protic solvents, that is, solvents free of groups such as hydroxyl represented by the alcohols. These solvents are characterized by at least partial solubility of the reactants in the solvent. Typical useful solvents include tetrahydrofuran, acetonitrile, chloroform, esters such as ethyl acetate, ethers such as dioxane, and even hydrocarbon solvents such as toluene and the like.

The molar ratios of the reactants normally used are about one mol of the substituted phenylphosphorodichloridite, one mol of water and two mols of the amine. While these proportions may be varied within a range of about 1 to 0.8-2.0 to 0.5-10 better yields are obtained when the 1:1:2 mol ratio is generally observed. Of course, an excess of any reactant may be used but the yield will depend on there being at least one mol of water and one mole of amine present.

The reaction is quite rapid and usually is conducted at about 0° C. to control the reaction rate, although the reaction temperature may vary from about −10° C. to 25° C. The reaction products prepared in accordance with this process normally need only be filtered as the reaction product is dissolved in the solvent, the solvent is evaporated and the resulting dry product washed, as with a mild aqueous alkaline solution, then washed with water and dried.

The structures of the 2,4,6-tris(substituted phenoxy)-1,3,5,2,4,6-trioxatriphosphorinanes of this invention were confirmed by infrared and nuclear magnetic resonance spectra. Molecular weights were determined and confirmed by field desorption mass spectra (FD/MS) and fast atom bombardment mass spectra (FAB/MS) or Vapor Phase Osmometry (VPO). In some cases elemental analysis for carbon, hydrogen and phosphorus was done and the amounts found were consistent with the formula of the material.

EXAMPLE I 2,4,6-tris(2,4,6-tri-t-butylphenoxy)-1,3,5,2,4,6-trioxatriphosphorinane 6.0 grams (0.017 mol) of 2,4,6-tri-t-butylphenylphosphorodichloridite and 3.34 grams (0.033 mol) of triethylamine were dissolved in 100 ml of tetrahydrofuran, and the solution was cooled to 0°–5° C. 0.30 gram (0.017 mol) of water was added to the solution and the mixture was stirred for 0.5 hour. The resulting reaction mixture was filtered and the filtrate was evaporated to a dry white glass. The glassy product was stirred three times with saturated aqueous sodium bicarbonate solution for ten minutes, each was then filtered, washed with water and air dried to provide the white solid product in about 70% yield. Two recrystallizations from ethyl acetate gave crystals, mp 226°–244° C., density 1.14. Calculated for $C_{18}H_{29}PO_2$: C, 70.10; H, 9.48; P, 10.04. Found: C, 69.83; H, 9.45; P, 10.0. VPO molecular weight (in $CHCl_3$ at 45° C.): 960 (actual 925.206). FD/MS: Mass numbers 308

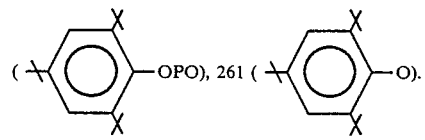

IR(Nujol) 950 cm$^{-1}$ (P-O), 820–840 cm$^{-1}$. $^1$H NMR(CDCl$_3$): δ1.28 (S,9H), 1.32 (S,18H), 1.35 (S, 18H), 1.49 (S, 36H), 7.29 (S, 2H), 7.33 (S, 4H). $^{31}$P NMR(CDCl$_3$): δ119.4 (d,J=10-11, 2P), 128.1 (t,J=10-11, 1P).

EXAMPLE II 2,4,6-tris(2,6-di-t-butyl-4-methylphenoxy)-1,3,5,2,4,6-trioxatriphosphorinane 6.0 grams (0.019 mol) of 2,6-di-t-butyl-4-methylphenylphosphorodichloridite and 3.78 grams (0.037 mol) of triethylamine were dissolved in 100 ml of tetrahydrofuran, and the solution was cooled to 0°–5° C. 0.34 gram (0.019 mol) of water was added to the solution and the mixture was stirred for 0.5 hour. The resulting reaction mixture was filtered and the filtrate was evaporated to dry white glass. The dry product was stirred twice with saturated aqueous sodium bicarbonate solution for ten minutes, filtered, washed with water and air dried to provide the white solid (4.04 grams). After washing in methanol, the solid had a mp 170°–184° C. Calculated for $C_{15}H_{23}O_2P$: C, 67.65; H, 8.71; P, 11.63. Found: C, 67.7; H, 8.68; P, 11.53. FD/MS: 799 (actual 798.96), 266

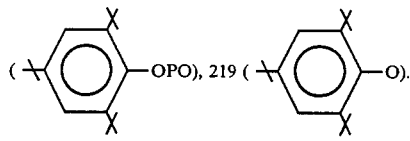

FAB/MS: 799. IR (Nujol) 950, 930 (P-O), 848, 820 cm$^{-1}$. $^1$H NMR(CDCl$_3$): δ1.35 (S,18H), 1.47 (S, 36H), 2.26 (S, 3H), 2.29 (S, 6H), 7.07 (S, 2H), 7.11 (S, 4H). $^{31}$P NMR (CDCl$_3$): δ120.0 (d,J=10, 2P), 127.9 (t,J=10, 1P).

EXAMPLE III 2,4,6-tris(2,6-di-t-butylphenoxy)-1,3,5,2,4,6-trioxatriphosphorinane 2.3 grams (0.0075 mol) of 2,6-di-ti-butylphenylphosphorodichloridite and 1.52 grams (0.015 mol) of triethylamine were dissolved in 50 ml of tetrahydrofuran, and the solution was cooled to 0°–5° C. 0.13 gram (0.0075 mol) of water was added to the stirred solution and the mixture was stirred for 0.5 hour. The resulting reaction mixture was filtered and the filtrate was evaporated to yellow glass. The glassy product was stirred twice with saturated aqueous sodium bicarbonate solutions for ten minutes, was then filtered, washed with water and air dried to provide the off-white solid product, mp 115°–132° C. in about 60% yield. Calculated for C$_{14}$H$_{21}$O$_2$P: C, 66.65; H, 8.39; P, 12.28. Found: C, 66.36; H, 8.46; P, 12.23. FD/MS: 758 (actual 757). IR (Nujol) 955, 932 (P-O), 848, 820 cm$^{-1}$. $^1$HNMR(CDCl$_3$): δ1.36 (S, 18H), 1.49 (s, 36H), 7.02 (m, 3H), 7.30 (m, 6H). $^{31}$PNMR(CDCl$_3$): 119.7 (d,J=10, 2P), 127.5 (t,J=10, 1P).

EXAMPLE IV 2,4,6-tris(2,6-di-t-butyl-4-ethylphenoxy)-1,3,5,2,4,6-trioxatriphosphorinane 2.0 grams (0.006 mol) of 2,6-di-t-butyl-4-ethylphenylphosphorodichloridite and 1.21 grams (0.012 mol) of triethylamine were dissolved in 50 ml of dry tetrahydrofuran, and the solution was cooled to 0°–5° C. 0.11 gram (0.006 mol) of water was added to the solution and the mixture was stirred for 0.5 hour. The resulting reaction mixture was filtered and the filtrate was evaporated to dry white glass. The dry product was dissolved in chloroform and was washed with saturated aqueous sodium bicarbonate solution, filtered, washed with water and dried to provide an off-white solid (0.8 gram). The melting point was 149°–155° C. from acetonitrile. Found C-67.62, H-8.88 and P-10.91 by analysis, calculated from C$_{16}$H$_{25}$O$_2$P, C-68.53, H-8.99 and P-11.05. $^1$HNMR(CDCl$_3$): 1.20(t,J=7.60) and 1.23 (t,J=7.60), 9H; 1.35 (S, 18H); 1.48 (S, 36H); 2.56 (q,J=7.60) and 2.59 (q,J=7.60), 6H; 7.09 (S, 2H); 7.13 (S, 4H).

EXAMPLE V 2,4,6-tris(2,6-di-t-butyl-4-n-butylphenoxy)-1,3,5,2,4,6-trioxatriphosphorinane 11.75 grams (0.032 mol) of 2,6-di-t-butyl-4-butylphenylphosphorodichloridite and 6.59 grams (0.0647 mol) of triethylamine were dissolved in 100 ml of tetrahydrofuran (THF), and the solution was cooled to 0°–5° C. 0.58 gram (0.032 mol) of water in 10 ml THF was added dropwise to the stirred solution and the mixture was stirred for 0.5 hour. The resulting reaction mixture was filtered and the filtrate was evaporated to an off-white glass. The glassy product was stirred in acetonitrile for 0.5 hour, was then filtered, and dried to provide a white solid product having a melting point of 137°–146° C. Calculated C-70.10, H-9.48, P-10.04 in C$_{18}$H$_{29}$O$_2$P: found C-70.17, H-9.44, and P-9.75. $^1$H NMR (CDCl$_3$): 0.93 and 0.94 (t, J=7.2, 9H), 1.34 (S, 18H), 1.48 (S, 36H), 1.12–1.63 (m, 12H), 2.51 and 2.55 (t, J=7.4, 6H), 7.07 (S, 2H), 7.11 (S, 4H).

EXAMPLE VI 2,4,6-tris(2,6-di-t-butyl-4-carbomethoxyphenoxy)-1,3,5,2,4,6-trioxatriphosphorinane 8.0 grams (0.022 mol) of 2,6-di-t-butyl-4-carbomethoxyphenylphosphorodichloridite and 4.43 grams (0.044 mol) of triethylamine were dissolved in 100 ml of tetrahydrofuran, and the solution was cooled to 0°–5° C. 0.39 gram (0.022 mol) of water in 10 ml THF was added dropwise to the solution and the mixture was stirred for 0.5 hour. The resulting reaction mixture was filtered and the filtrate was evaporated to a light yellow solid. The dry product was stirred with ethyl acetate, filtered, and dried to provide the white solid, melting point 185°–200° C.

EXAMPLE VII 2,4,6-tris[2,6-di-t-butyl-4-(2-carboethoxyethyl)phenoxy]-1,3,5,2,4,6-trioxatriphosphorinane 5.5 grams (0.013 mol) of 2,6-di-t-butyl-4-(2-carboethoxyethylphenylphosphorodichloridite and 2.73 grams (0.027 mol) of triethylamine were dissolved in 50 ml of tetrahydrofuran, and the solution was cooled to 0°–5° C. 0.24 grams (0.013 mol) of water in 10 ml THF was added to the stirred solution and the mixture was stirred for 0.5 hour. The resulting reaction mixture was filtered and the filtrate was evaporated to a yellow oil. IR(neat)1728 cm$^{-1}$ (C=O), 930 cm$^{-1}$ (P-O), 820 cm$^{-1}$.

EXAMPLE VIII 2,4,6-tris[2,6-di-t-butyl-4-(1-methyl-1-diethylcarbamoylethyl)phenoxy]-1,3,5,2,4,6-trioxatriphosphorinane 2.0 grams (0.004 mol) of 2,6-di-t-butyl-4-(1-methyl-1-diethylcarbamoylethyl)phenylphosphorodichloridite and 0.9 grams (0.009 mol) of triethylamine were dissolved in 45 ml of tetrahydrofuran, and the solution was cooled to 0°–5° C. 0.08 gram (0.004 mol) of water in THF was added dropwise to the solution and the mixture was stirred for 0.5 hour. The resulting reaction mixture was filtered and the filtrate was evaporated to dry white glass. IR(neat) 1640 cm$^{-1}$ (C=O), 930 cm$^{-1}$ (P-O), 818 cm$^{-1}$. The NMR spectrum was consistent with the proposed structure.

Test samples of 2,4,6-tris(substituted phenoxy)-1,3,5,2,4,6-trioxatriphosphorinanes in polypropylene were prepared by mixing the stabilizer compounds with polypropylene in a Brabender Plasticorder fitted with a Cam-Head (mixing chamber). The polypropylene was first masticated for 1½ minutes at 190° C. Then the stabilizer was added, followed by 3 minutes additional mixing. The mass was removed and pressed into 20 mil thick sheets. From these sheets 1"×1" plaques were cut for oven aging.

Thermal/oxidative stability (oven aging) testing consisted of aging the samples in triplicate in an air-circulating oven at 125° C. The time to catastrophic crumbling (failure) of the plaque was measured and reported as days to failure.

Each sample contained 0.1 weight part of 2,4,6-tris(-substituted phenoxy)-1,3,5,2,4,6-trioxatriphosphorinane per 100 weight parts of polypropylene. The following results were obtained.

2,4,6-tris(2,4,6-tri-t-butylphenoxy)-1,3,5,2,4,6-trioxatriphosphorinane ... 10⅓ days 2,4,6-tris(2,6-di-t-butyl-4-methylphenoxy)-1,3,5,2,4,6-trioxatriphosphorinane ... 9⅓ days 2,4,6-tris(2,6-di-t-butylphenoxy)-1,3,5,2,4,6-trioxatriphosphorinane ... 12⅔ days The 2,4,6-tris(substituted phenoxy)-1,3,5,2,4,6-trioxatriphosphorinanes form particularly useful stabilizer combinations with hindered or partially hindered phenols. Typical of such phenols are the hydroxyphenylalkylenyl isocyanurates such as the symmetrical tris(3,5-di-t-alkyl-4-hydroxybenzyl)isocyanurates described in detail hereinafter; tetrakis[methylene 3-(3′,5′-dialkyl-4′-hydroxyphenyl)propanoate]methanes wherein the alkyl groups contain 1 to 8 carbon atoms, such as tetrakis[methylene 3-(3′,5′-di-t-butyl-4′-hydroxyphenyl)propanoate]methane; alkyl 3-(3′,5′-di-t-butyl-4′-hydroxyphenyl)propionates wherein the alkyl groups contain 1 to 18 carbon atoms, such as octadecyl 3-(3′,5′-di-t-butyl-4-hydroxyphenyl)propionate; 1,3,5-trimethyl-2,4,6-tris[3,5-dialkyl-4-hydroxybenzyl]benzene wherein the alkyl groups contain 1 to 5 carbon atoms, such as 1,3,5-trimethyl-2,4,6-tris[3,5-di-t-butyl-4-hydroxybenzyl]benzene; 1,3,5-tris(3,5-di-t-butyl-4-hydroxy-hydrocinnamoylethyl)-s-triazine-2,4,6(1H,3H,5H)-trione; 2,2′-alkylidene bis(4,6-dialkylphenols) wherein the alkyl group contains 1 to 8 carbon atoms, such as 2,2′-methylene bis(4,6-di-t-butylphenol), 2,2′-ethylidene bis(4,6-di-t-butylphenol), and 2,2′-methylene bis(4-methyl-6-t-butylphenol); and the like.

The hydroxyphenylalkyleneyl isocyanurate compounds used in combination with the 2,4,6-tris(substituted phenoxy)-1,3,5,2,4,6-trioxatriphosphorinane of this invention have the formula

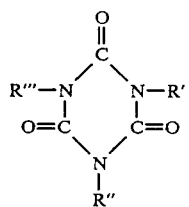

wherein R′ is a hydroxyphenylalkyleneyl radical of the formula

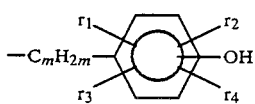

where m is 1 to 4, $r_1$ is an alkyl radical having 1 to 18 carbon atoms and is positioned immediately adjacent to the hydroxy group on the ring; $r_2$, $r_3$ and $r_4$ are hydrogen or an alkyl radical containing 1 to 18 carbon atoms; and R″ and R‴ are hydrogen, alkyl radical containing 1 to 18 carbon atoms, or are the same as R′. A more preferred compound is when R″ and R‴ are equal to R′, i.e., all the R groups are hydroxyphenylalkyleneyl radicals, and $r_1$ is a t-alkyl radical containing from 4 to about 12 carbon atoms, $r_2$ is a t-alkyl radical containing from 4 to about 12 carbon atoms, $r_3$ and $r_4$ are hydrogen, and m=1.

Even more preferred are the symmetrical tris(3,5-di-tert-alkyl-4-hydroxybenzyl)isocyanurates of the formula

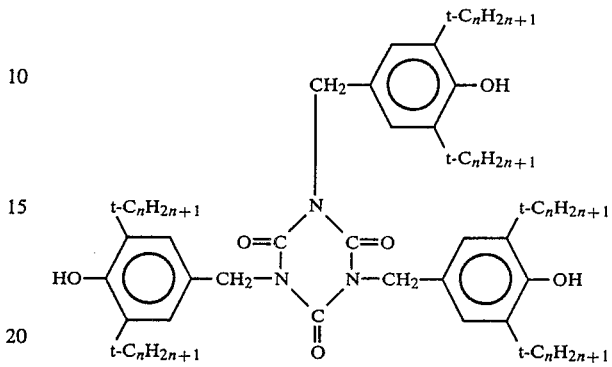

wherein n is 4 to 8.

Examples of the 4-hydroxybenzyl isocyanurate compounds are: tris-3-t-butyl-4-hydroxybenzyl)isocyanurate, tris-(3-cetyl-4-hydroxybenzyl)isocyanurate, tris(3,5-dimethyl-4-hydroxybenzyl)isocyanurate, tris-(3-methyl-5-isopropyl-4-hydroxybenzyl)isocyanurate, tris-(3,5-di-t-butyl-4-hydroxybenzyl)isocyanurate, tris(3-t-butyl-5-t-amyl-4-hydroxybenzyl)isocyanurate, tris-[3,5-di(1-methyl-1-ethylpropyl)-4-hydroxybenzyl]isocyanurate, tris-[3,5-di-(1,1,2,2-tetramethylpropyl)-4-hydroxybenzyl]isocyanurate, bis(3,5-dimethyl-4-hydroxybenzyl)isocyanurate, (3-methyl-4-hydroxybenzyl)isocyanurate, (3-t-butyl-4-hydroxybenzyl)isocyanurate and the like. Reference is made to U.S. Pat. No. 3,531,483 which discloses isocyanurate compounds encompassed by this invention. This disclosure of this patent is incorporated herein by reference.

The amount of 2,4,6-tris(substituted phenoxy)-1,3,5,2,4,6-trioxatriphosphorinane used may vary from about 0.01 to 10 weight parts per 100 weight parts of material to be stabilized. More usually about 0.1 to 5.0 parts are used for mixtures with the hindered phenols such as hydroxyphenylalkyleneyl isocyanurates. The hindered phenols, i.e., hydroxyphenylalkyleneyl isocyanurate compounds, are used at a level from about 0.01 part to about 5 parts by weight, and more preferably at from about 0.05 part to about 3 parts by weight per 100 parts by weight of the organic material. The 2,4,6-tris(substituted phenoxy)-1,3,5,2,4,6-trioxatriphosphorinane compound is employed at similar levels, i.e., from about 0.01 part to 5 parts and preferably at about 0.05 part to about 3 parts by weight per 100 parts by weight of organic material. Thus the combined weight of the compounds is normally from about 0.02 part to about 10 parts and more preferably from about 0.05 to 5 parts by weight per 100 parts by weight of organic material. The hydroxyphenylalkyleneyl isocyanurate can be used in from about 10:1 to 1:10 weight ratio of isocyanurate compound to the 2,4,6-tris(substituted phenoxy)-1,3,5,2,4,6-trioxatriphosphorinanes. Excellent results are obtained at about a 3:1 to 1:3 weight ratio. A 1:1 weight ratio of the compounds provides effective stabilization of organic materials.

To demonstrate the unexpected synergistic enhancement of antioxidant activity obtained when the 2,4,6- tris(substituted phenoxy)-1,3,5,2,4,6-trioxatriphosphorinanes of this invention are combined with hydroxyphenylalkyleneyl isocyanurates, test samples of polypropylene with 0.05 weight part each of tris(3,5-di-t-butyl-4-hydroxybenzyl)isocyanurate and the 2,4,6-tris(-substituted phenoxy)-1,3,5,2,4,6-trioxatriphosphorinane listed below were prepared and tested in the air oven until failure. The results obtained were as follows:

2,4,6-tris(2,4,6-tri-t-butylphenoxy)-1,3,5,2,4,6-trioxatriphosphorinane . . . 112 days 2,4,6-tris(2,6-di-t-butyl-4-methylphenoxy)-1,3,5,2,4,6-trioxatriphosphorinane . . . 128 days 2,4,6-tris(2,6-di-t-butylphenoxy)-1,3,5,2,4,6-trioxatriphosphorinane . . . 90 days.

A sample of polypropylene containing 0.1 weight part of tris(3,5-di-t-butyl-4-hydroxybenzyl)isocyanurate failed only after about 25⅓ days. This is to be contrasted to the synergistic combination above wherein only 0.05 weight parts of the tris(3,5-di-t-butyl-4-hydroxybenzyl)isocyanurate in combination with 0.05 weight part of the 2,4,6-tris(substituted phenoxy)-1,3,5,2,4,6-trioxatriphosphorinane did not fail for periods of more than 100 days! These values are to be contrasted with commercial phosphorous containing stabilizers. With 0.1 weight parts of 2,4-di-t-butylphenyl pentaerythritol diphosphite, a value of 12 days was obtained, and with 0.05 weight part each of this diphosphite and the isocyanurate, the samples began to show degradiation after 49 days, with total degradation observed at 62 days. With 0.1 weight part of distearyl pentaerythritol diphosphite, only a value of 3⅓ days was obtained. With 0.05 weight part each of this diphosphite and the isocyanurate, degradation was observed after 63 days, with total degradation occurring at 75 days. In contrast, the materials of this invention did not show any signs of degradation after 100 days when combined with the isocyanurate in amounts of 0.05 weight parts each.

The combination of isocyanurate compound and the 2,4,6-tris(substituted phenoxy)-1,3,5,2,4,6-trioxatriphosphorinane compounds as defined herein provide exceptional heat stability to polyolefin polymers. The combination is especially useful for the stabilization of α-monoolefin homopolymers and copolymers, wherein the α-monoolefin contains 2 to about 8 carbon atoms. High and low-density polyethylene, isotactic and atactic polypropylene, polyisobutylene, and poly(4-methyl-1-pentene) have excellent resistance to heat and oxygen when stabilized with the combinations of the present invention. Ethylene-propylene copolymers and ethylene-propylene terpolymers, generally containing less than about 10 percent by weight of one or more monomers containing multiple unsaturation provided, for example, by 1,4-hexadiene, dimethyl-1,4,9-decatriene, dicyclopentadiene, vinyl norborene, ethylidene norborene, and the like, also provide excellent ageing using the combination.

Other organic materials which can be stabilized in accordance with the present invention include both natural and synthetic polymers. For example, the stabilizers are useful for the stabilization of cellulosic materials; natural rubber, halogenated rubber, conjugated diene polymers, as, for instance, polybutadiene, copolymers of butadiene with styrene, acrylonitrile, acrylic acid, alkyl acrylates or methacrylates, methyl vinyl ketone, vinyl pyridine, etc.; polyisoprene, polychloroprene, and the like; vinyl polymers such as poly(vinyl chloride), poly(vinylidene chloride), copolymers of vinyl chloride with vinylidene chloride, polyvinyl acetate, copolymers or vinyl halide with butadiene, styrene, vinyl esters, α,β-unsaturated ketones and aldehydes, and the like; homopolymers and copolymers of acrylic monomers such as acrylic acid, methacrylic acid, methyl acrylate, methyl methacrylate, ethyl acrylate, 3-ethylhexyl acrylate, acrylamide, methacrylamide, N-methylol-acrylamide, haloacrylates, acrylonitrile, methacrylonitrile, haloacrylates, and the like; epihalohydrin polymers; polyether- or polyol-derived polyurethanes; acetal homopolymers and copolymers; polycarbonates; polyesters such as those derived from maleic, fumaric, itaconic, or terephthalic anhydrides; for example, polyethylene terephthalate; polyamides such as those derived from the reaction of hexamethylenediamine with adipic or sebacic acid; epoxy resins such as those obtained from the condensation of epichlorohydrin with bisphenols; ring opened olefin polymers and the like. Polymer blends, that is, physical admixture of two or more polymers may also be stabilized in accordance with the present invention.

In addition to polymeric materials, the present compounds may stabilize a wide variety of other organic materials. Such compounds include: waxes, synthetic and petroleum-derived lubricating oils and greases; animal oils such as, for example, fat, tallow, lard, cod-liver oil, sperm oil; vegetable oils such as castor, linseed, peanut, palm, cotton seed, and the like; fuel oil; diesel oil, gasoline and the like.

The compounds are readily incorporated into materials to be patented by dissolving or dispersing them with the materials, in liquids, dispersions, solutions, and solid forms. If the material is a solid, especially a polymeric solid such as rubber or a plastic, the compounds can be admixed using mixers such as Banburys, extruders, two-roll mills, and the like, following conventional techniques. One way to disperse the compounds in plastic materials is to dissolve or suspend the compounds in a solvent or diluent, mix the mixture with a plastic in powder or solution form, and then evaporate the solvent.

Compositions containing the novel combination of compounds can also contain other known compounding ingredients such as fillers like carbon black, silica, metal carbonates, talc, and the like; pigments and colorants; curative ingredients like sulfur and peroxides, and vulcanization accelerators; fungicides; processing aids, reinforcing agents and standard ingredients known to the art. Other ingredients known in the art as ultra violet light, thermal and/or oxidative stabilizers can also be used in the stabilized compositions.

I claim:

1. A composition comprising organic materials subject to degradation and stabilizing amounts of 2,4,6-tris(substituted phenoxy)-1,3,5,2,4,6-trioxatriphosphorinanes having the structural formula

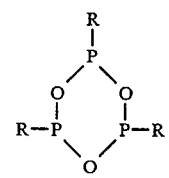

wherein R is

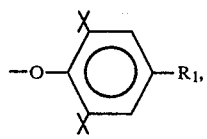

+ is t-butyl or t-pentyl and $R_1$ is hydrogen, primary, secondary, and tertiary alkyl radicals containing 1 to 9 carbon atoms, cycloalkyl radicals containing 3 to 6 carbon atoms, halogen, cyano, alkoxy radicals containing 1 to 8 carbon atoms, phenyl, $COOR_2$ esters wherein $R_2$ is an alkyl radical containing 1 to 8 carbon atoms, $-CH_2CH_2COOR_3$ wherein $R_3$ is an alkyl radical containing 1 to 18 carbon atoms, and $-C(CH_3)_2CON(R_4)_2$ wherein $R_4$ is an alkyl radical containing 1 to 9 carbon atoms, and (2) hindered or partially hindered phenols selected from the group consisting of hydroxyphenylalkyleneyl isocyanurates, tetrakis[methylene 3-(3′,5′-dialkyl-4′-hydroxyphenyl)propanoate]methanes wherein the alkyl groups contain 1 to 8 carbon atoms, alkyl 3-(3′,5′-di-t-butyl-4′-hydroxyphenyl)propionates wherein the alkyl groups contain 1 to 18 carbon atoms, 1,3,5-trimethyl-2,4,6-tris[3,5-dialkyl-4-hydroxybenzyl]-benzene wherein the alkyl groups contain 1 to 5 carbon atoms, 1,3,5-tris(3,5-di-t-butyl-4-hydroxy-hydrocinnamoyloxyethyl)-s-triazine-2,4,6(1H,3H,5H)-trione, and 2,2′-alkylidene bis(4,6-dialkylphenols) wherein the alkyl groups contain 1 to 8 carbon atoms.

2. A stabilizer composition of claim 1 wherein in (1) + is t-butyl, $R_1$ is hydrogen, alkyl radicals containing 1 to 4 carbon atoms, and $-COOR_2$, $-CH_2CH_2COOR_3$, $-C(CH_3)_2CON(R_4)_2$ wherein $R_2$, $R_3$ and $R_4$ are alkyl radicals containing 1 to 4 carbon atoms, and (2) is selected from the group consisting of 1,3,5-tris(3,5-di-t-butyl-4-hydroxybenzyl)isocyanurates, tetrakis[methylene 3-(3′,5′-di-t-butyl-4′-hydroxyphenyl)-propanoate]methane, octadecyl 3-(3′,5′-di-t-butyl-4-hydroxyphenyl)propionate, 1,3,5-trimethyl-2,4,6-tris[3,5-di-t-butyl-4-hydroxybenzyl]benzene, 1,3,5-tris(3,5-di-t-butyl-4-hydroxy-hydrocinnamoyloxyethyl)-s-triazine-2,4,6(1H,3H,5H)-trione, 2,2′-methylene bis(4,6-di-t-butylphenol), 2,2′-ethylidene bis (4,6-di-t-butylphenol), and 2,2′-methylene bis(4-methyl-6-t-butylphenol).

3. A composition of claim 1 wherein in (2) the hydroxyphenylalkyleneyl isocyanurates have the formula

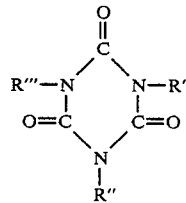

wherein R′ is a hydroxyphenylalkyleneyl radical of the formula

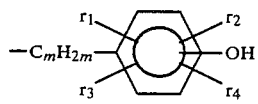

where m is 1 to 4; $r_1$ is an alkyl radical having 1 to 18 carbon atoms and is positioned immediately adjacent to the hydroxy group on the ring; $r_2$, $r_3$ and $r_4$ are hydrogen or alkyl radicals containing 1 to 18 carbon atoms; and R″ and R‴ are hydrogen, an alkyl radical containing 1 to 18 carbon atoms, or are the same as R′.

4. A composition of claim 3 wherein said organic material is a polymer, in (1) + is t-butyl, $R_1$ is hydrogen, alkyl radicals containing 1 to 4 carbon atoms, alkoxy radicals containing 1 to 4 carbon atoms, $-COOR_2$, $-CH_2CH_2COOR_3$ and $C(CH_3)_2CON(R_4)_2$ radicals wherein the $R_2$, $R_3$ and $R_4$ alkyl radicals contains 1 to 4 carbon atoms, and in (2) R″ and R‴ are equal to R′, $r_1$ is a tertiary alkyl radical containing 4 to 12 carbon atoms, $r_2$ is a t-alkyl radical containing 4 to 12 carbon atoms, $r_3$ and $r_4$ are hydrogen, and m is 1.

5. A composition of claim 4 wherein (2) has the formula

[Structure of isocyanurate with three $t$-$C_nH_{2n+1}$ substituted hydroxyphenyl-$CH_2$- groups attached to N of the triazine-trione ring]

wherein n is 4 to 8.

6. A composition of claim 5 wherein (2) is 1,3,5-tris(3,5-di-t-butyl-4-hydroxybenzyl)isocyanurate.

7. A composition of claim 6 wherein (1) is selected from the group consisting of 2,4,6-tris(2,6-di-t-butyl-4-methylphenoxy)-1,3,5,2,4,6-trioxatriphosphorinane, 2,4,6-tris(2,6-di-t-butyl-4-ethylphenoxy)-1,3,5,2,4,6-trioxatriphosphorinane, 2,4,6-tris(2,6-di-t-butyl-4-propylphenoxy)-1,3,5,2,4,6-trioxatriphosphorinane, 2,4,6-tris(2,6-di-t-butyl-4-isopropylphenoxy)-1,3,5,2,4,6-trioxatriphosphorinane, 2,4,6-tris(2,6-di-t-butyl-4-n-butylphenoxy)-1,3,5,2,4,6-trioxatriphosphorinane, 2,4,6-tris(2,6-di-t-butyl-4-isoamylphenoxy)-1,3,5,2,4,6-trioxatriphosphorinane, 2,4,6-tris(2,6-di-t-butyl-4-methoxyphenoxy)-1,3,5,2,4,6-trioxatriphosphorinane, 2,4,6-tris(2,6-di-t-butyl-4-ethoxyphenoxy)-1,3,5,2,4,6-trioxatriphosphorinane, 2,4,6-tris(2,6-di-t-butyl-4-carbomethoxyphenoxy)-1,3,5,2,4,6trioxatriphosphorinane, 2,4,6-tris(2,4,6-tri-t-butylphenoxy)-1,3,5,2,4,6-trioxatriphosphorinane, 2,4,6-tris[2,6-di-t-butyl-4(2-carboethoxyethyl)phenoxy]-1,3,5,2,4,6-trioxatriphosphorinane, 2,4,6-tris[2,6-di-t-butyl-4-(1-methyl-1-diethylcarbamoylethyl)phenoxy]-1,3,5,2,4,6-trioxatriphosphorinane, and 2,4,6-tris[2,6-di-t-butyl-4-(2-carbooctadecyloxy-ethyl)-phenoxy]-1,3,5,2,4,6-trioxatriphosphorinane.

8. Compositions comprising organic materials subject to degradation and stabilizing amounts of 2,4,6-tris(substituted phenoxy)-1,3,5,2,4,6-trioxatriphosphorinane having the structural formula

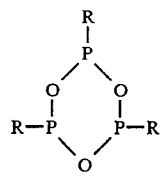

wherein R is

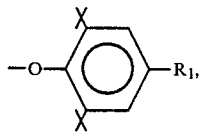

+ is t-butyl, or t-pentyl and $R_1$ is hydrogen, primary, secondary, and tertiary alkyl radicals containing 1 to 9 carbon atoms, cycloalkyl radicals containing 3 to 6 carbon atoms, halogen, cyano, alkoxy radicals containing 1 to 8 carbon atoms, phenyl, $COOR_2$ esters wherein $R_2$ is an alkyl radical containing 1 to 8 carbon atom, —$CH_2CH_2COOR_3$ wherein $R_3$ is an alkyl radical containing 1 to 18 carbon atoms, and —$C(CH_3)_2CON(R_4)_2$ wherein $R_4$ is an alkyl radical containing 1 to 9 carbon atoms.

9. A composition of claim 8 wherein + is t-butyl and $R_1$ is hydrogen, alkyl radicals containing 1 to 4 carbon atoms, alkoxy radicals containing 1 to 4 carbon atoms, and —$COOR_2$, —$CH_2CH_2COOR_3$ and —$C(CH_3)_2CON(R_4)_2$ radicals wherein the $R_2$, $R_3$ and $R_4$ alkyl radicals contain 1 to 4 carbon atoms.

10. A composition of claim 9 wherein said organic material is a polymer and the 2,4,6-tris(substituted phenoxy)-1,3,5,2,4,6-trioxatriphosphorinane is selected from the group consisting of 2,4,6-tris(2,6-di-t-butyl-4-methylphenoxy)-1,3,5,2,4,6-trioxatriphosphorinane, 2,4,6-tris(2,6-di-t-butyl-4-ethylphenoxy)-1,3,5,2,4,6-trioxatriphosphorinane, 2,4,6-tris(2,6-di-t-butyl-4-propylphenoxy)-1,3,5,2,4,6-trioxatriphosphorinane, 2,4,6-tris(2,6-di-t-butyl-4-isopropylphenoxy)-1,3,5,2,4,6-trioxatriphosphorinane, 2,4,6-tris(2,6-di-t-butyl-4-n-butylphenoxy)-1,3,5,2,4,6-trioxatriphosphorinane, 2,4,6-tris(2,6-di-t-butyl-4-isoamylphenoxy)-1,3,5,2,4,6-trioxatriphosphorinane, 2,4,6-tris(2,6-di-t-butyl-4-methoxyphenoxy)-1,3,5,2,4,6-trioxatriphosphorinane, 2,4,6-tris(2,6-di-t-butyl-4-ethoxyphenoxy)-1,3,5,2,4,6-trioxatriphosphorinane, 2,4,6-tris(2,6-di-t-butyl-4-carbomethoxyphenoxy)-1,3,5,2,4,6-trioxatriphosphorinane, 2,4,6-tris(2,4,6-tri-t-butylphenoxy)-1,3,5,2,4,6-trioxatriphosphorinane, 2,4,6-tris[2,6-di-t-butyl-4-(2-carboethoxyethyl)phenoxy]-1,3,5,2,4,6-trioxatriphosphorinane, 2,4,6-tris[2,6-di-t-butyl-4-(1-methyl-1-diethylcarbamoylethyl)phenoxy]-1,3,5,2,4,6-trioxatriphosphorinane, and 2,4,6-tris[2,6-di-t-butyl-4-(2-carbooctadecyloxyethyl)phenoxy]-1,3,5,2,4,6-trioxatriphosphorinane.

11. A stabilizer composition for organic materials comprising 2,4,6-tris(substituted phenoxy)-1,3,5,2,4,6-trioxatriphosphorinanes having the structural formula

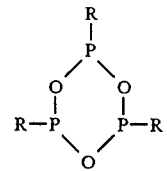

wherein R is

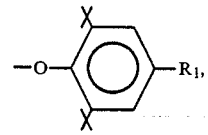

+ is t-butyl or t-pentyl and $R_1$ is hydrogen, primary, secondary, and tertiary alkyl radicals containing 1 to 9 carbon atoms, cycloalkyl radicals containing 3 to 6 carbon atoms, halogen, cyano, alkoxy radicals containing 1 to 8 carbon atoms, phenyl, $COOR_2$ esters wherein $R_2$ is an alkyl radical containing 1 to 8 carbon atoms, —$CH_2CH_2COOR_3$ wherein $R_3$ is an alkyl radical containing 1 to 18 carbon atoms, and —$C(CH_3)_2CON(R_4)_2$ wherein $R_4$ is an alkyl radical containing 1 to 9 carbon atoms, and (2) hindered or partially hindered phenols selected from the group consisting of hydroxyphenylalkyleneyl isocyanurates, tetrakis[methylene 3-(3',5'-dialkyl-4'-hydroxyphenyl)propanoate]methanes wherein the alkyl groups contain 1 to 8 carbon atoms, alkyl 3-(3',5'-di-t-butyl-4'-hydroxyphenyl)propionates wherein the alkyl groups contain 1 to 18 carbon atoms, 1,3,5-trimethyl-2,4,6-tris[3,5-dialkyl-4-hydroxybenzyl]benzene wherein the alkyl groups contain 1 to 5 carbon atoms, 1,3,5-tris(3,5-di-t-butyl-4-hydroxy-hydrocinnamoyloxyethyl)-s-triazine-2,4,6(1H,3H,5H)-trione and 2,2'-alkylidene bis(4,6-dialkylphenols) wherein the alkyl groups contain 1 to 8 carbon atoms.

12. A stabilizer composition of claim 11 wherein in (1) + is t-butyl, $R_1$ is hydrogen, alkyl radicals containing 1 to 4 carbon atoms, alkoxy radicals containing 1 to 4 carbon atoms, and —$COOR_2$, —$CH_2CH_2COOR_3$, —$C(CH_3)_2CON(R_4)$ radicals wherein said $R_2$, $R_3$, and $R_4$ alkyl radicals contain 1 to 4 carbon atoms, and (2) is selected from the group consisting of 1,3,5-tris(3,5-di-t-butyl-4-hydroxybenzyl)isocyanurate, tetrakis[methylene 3-(3',5'-di-t-butyl-4'-hydroxyphenyl)propanoate]methane, octadecyl 3-(3',5'-di-t-butyl-4-hydroxyphenyl)propionate, 1,3,5-trimethyl-2,4,6-tris[3,5-di-t-butyl-4-hydroxybenzyl]benzene; 1,3,5-tris(3,5-di-t-butyl-4-hydroxy-hydrocinnamoyloxyethyl)-s-triazine-2,4,6-(1H,3H,5H)-trione, 2,2'-methylene bis(4,6-di-t-butylphenol), 2,2'-ethylidene bis(4,6-di-t-butylphenol), and 2,2'-methylene bis(4-methyl-6-t-butylphenol).

13. A stabilizer composition of claim 11 wherein in (2) the hydroxyphenylalkyleneyl isocyanurates have the formula

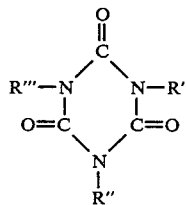

wherein R' is a hydroxyphenylalkyleneyl radical of the formula

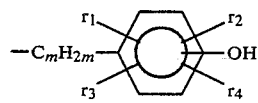

where m is 1 to 4; $r_1$ is an alkyl radical having 1 to 18 carbon atoms and is positioned immediately adjacent to the hydroxy group on the ring; $r_2$, $r_3$ and $r_4$ are hydrogen or alkyl radicals containing 1 to 18 carbon atoms; and R" and R'" are hydrogen, an alkyl radical containing 1 to 18 carbon atoms, or are the same as R'.

14. A stabilizer composition of claim 13 wherein in (1) + is t-butyl, $R_1$ is hydrogen, alkyl radicals containing 1 to 4 carbon atoms, alkoxy radicals containing 1 to 4 carbon atoms, and —COOR$_2$, —CH$_2$CH$_2$COOR$_3$, —C(CH$_3$)$_2$CON(R$_4$)$_2$ radicals wherein said $R_2$, $R_3$ and $R_4$ alkyl radicals contain 1 to 4 carbon atoms, and in (2) R" and R'" are equal to R', and $r_1$ is a t-alkyl radical containing from 4 to about 12 carbon atoms, $r_2$ is a t-alkyl radical containing from 4 to about 12 carbon atoms, $r_3$ and $r_4$ are hydrogen, and m is 1.

15. A stabilizer composition of claim 14 wherein (2) has the formula

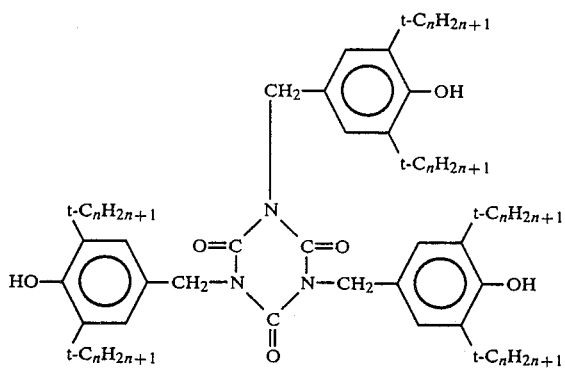

where n is 4 to 8.

16. A stabilizer composition of claim 14 wherein (1) is selected from the group consisting of 2,4,6-tris(2,6-di-t-butyl-4-methylphenoxy)-1,3,5,2,4,6-trioxatriphosphorinane, 2,4,6-tris(2,6-di-t-butyl-4-ethylphenoxy)-1,3,5,2,4,6-trioxatriphosphorinane, 2,4,6-tris(2,6-di-t-butyl-4-propylphenoxy)-1,3,5,2,4,6-trioxatriphosphorinane, 2,4,6-tris(2,6-di-t-butyl-4-isopropylphenoxy)-1,3,5,2,4,6-trioxatriphosphorinane, 2,4,6-tris(2,6-di-t-butyl-4-n-butylphenoxy)-1,3,5,2,4,6-trioxatriphosphorinane, 2,4,6-tris(2,6-di-t-butyl-4-isoamylphenoxy)-1,3,5,2,4,6-trioxatriphosphorinane, 2,4,6-tris(2,6-di-t-butyl-4-methoxyphenoxy)-1,3,5,2,4,6-trioxatriphosphorinane, 2,4,6-tris(2,6-di-t-butyl-4-ethoxyphenoxy)-1,3,5,2,4,6-trioxatriphosphorinane, 2,4,6-tris(2,6-di-t-butyl-4-carbomethoxyphenoxy)-1,3,5,2,4,6-trioxatriphosphorinane, 2,4,6-tris(2,4,6-tri-t-butylphenoxy)-1,3,5,2,4,6-trioxatriphosphorinane, 2,4,6-tris[2,6-di-t-butyl-4-(2-carboethoxyethyl)phenoxy]-1,3,5,2,4,6-trioxatriphosphorinane, 2,4,6-tris[2,6-di-t-butyl-4-(1-methyl-1-diethylcarbamoylethyl)phenoxy]-1,3,5,2,4,6-trioxatriphosphorinane, and 2,4,6-tris[2,6-di-t-butyl-4-(2-carbooctadecyloxyethyl)phenoxy]-1,3,5,2,4,6-trioxatriphosphorinane.

17. A composition of claim 16 wherein (2) is 1,3,5-tris(3,5-di-t-butyl-4-hydroxybenzyl)isocyanurate.

18. 2,4,6-tris(substituted phenoxy)-1,3,5,2,4,6-trioxatriphosphorinanes having the structural formula

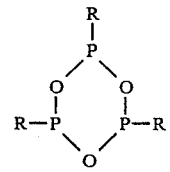

wherein R is

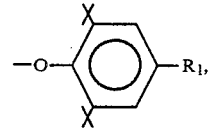

+ is t-butyl or t-pentyl and $R_1$ is hydrogen, primary, secondary, and tertiary alkyl radicals containing 1 to 9 carbon atoms, cycloalkyl radicals containing 3 to 6 carbon atoms, halogen, cyano, alkoxy radicals containing 1 to 8 carbon atoms, phenyl, —COOR$_2$ esters wherein $R_2$ is an alkyl radical containing 1 to 8 carbon atoms, —CH$_2$CH$_2$COOR$_3$ wherein $R_3$ is an alkyl radical containing 1 to 18 carbon atoms, and —C(CH$_3$)$_2$CON(R$_4$)$_2$ wherein $R_4$ is an alkyl radical containing 1 to 9 carbon atoms.

19. 2,4,6-tris(substituted phenoxy)-1,3,5,2,4,6-trioxatriphosphorinanes of claim 18 wherein + is t-butyl and $R_1$ is hydrogen, alkyl radicals containing 1 to 4 carbon atoms, alkoxy radicals containing 1 to 4 carbon atoms, —COOR$_2$, —CH$_2$CH$_2$COOR$_3$ and —C(CH$_3$)$_2$CON(R$_4$)$_2$ radicals wherein $R_2$, $R_3$ and $R_4$ are alkyl radicals containing 1 to 4 carbon atoms.

20. 2,4,6-tris(substituted phenoxy)-1,3,5,2,4,6-trioxatriphosphorinanes of claim 19 selected from the group consisting of 2,4,6-tris(2,6-di-t-butyl-4-methylphenoxy)-1,3,5,2,4,6-trioxatriphosphorinane, 2,4,6-tris(2,6-di-t-butyl-4-ethylphenoxy)-1,3,5,2,4,6-trioxatriphosphorinane, 2,4,6-tris(2,6-di-t-butyl-4-propylphenoxy)-1,3,5,2,4,6-trioxatriphosphorinane, 2,4,6-tris(2,6-di-t-butyl-4-isopropylphenoxy)-1,3,5,2,4,6-trioxatriphosphorinane, 2,4,6-tris(2,6-di-t-butyl-4-n-butylphenoxy)-1,3,5,2,4,6-trioxatriphosphorinane, 2,4,6-tris(2,6-di-t-butyl-4-iso-amylphenoxy)-1,3,5,2,4,6-trioxatriphosphorinane, 2,4,6-tris(2,6-di-t-butyl-4-methoxyphenoxy)-1,3,5,2,4,6-trioxatriphosphorinane 2,4,6-tris(2,6-di-t-butyl-1-4-ethoxyphenoxy)-1,3,5,2,4,6-trioxatriphosphorinane, 2,4,6-tris(2,6-di-t-butyl-4-carbomethoxyphenoxy)-1,3,5,2,4,6-trioxatriphosphorinane, 2,4,6-tris(2,4,6-tri-t-butylphenoxy)-1,3,5,2,4,6-trioxatriphosphorinane, 2,4,6-tris[2,6-di-t-butyl-4-(2-carboethoxyethyl)phenoxy]-1,3,5,2,4,6-trioxatriphosphorinane, 2,4,6- tris[2,6-di-t-butyl-4-(1-methyl-1-diethylcarbamoylethyl)phenoxy]-1,3,5,2,4,6-t-rioxatriphosphorinane, and 2,4,6-tris[2,6-di-t-butyl-4-(2-carbooctadecyloxyethyl)phenoxy]-1,3,5,2,4,6-trioxatriphosphorinane.

21. A method for making 2,4,6-tris(substituted phenoxy)-1,3,5,2,4,6-trioxatriphosphorinanes comprising reacting together 2,6-di-t-butylphenylphosphorodichloridite or a 2,6-di-t-butyl-4-substituted phenylphosphorodichloridite wherein the substitution at the 4-position is a primary, secondary or tertiary alkyl radical containing 1 to 9 carbon atoms, cycloalkyl radicals containing 3 to 6 carbon atoms, a halogen radical, a cyano radical, alkoxy radicals containing 1 to 8 carbon atoms, phenyl, —$COOR_2$, —$CH_2CHO_2COOR_3$ and —$C(CH_3)_2CON(R_4)_2$ radicals wherein $R_2$ and $R_3$ are alkyl radicals containing 1 to 8 carbon atoms, and $R_4$ is an alkyl radical containing 1 to 9 carbon atoms, with water and an amine.

22. A method of claim 21 wherein in the phosphorodichloridite the substitution at the 4- position is an alkyl radical containing 1 to 4 carbon atoms, an alkoxy radical containing 1 to 4 carbon atoms, —$COOR_2$, —$CH_2CH_2COOR_3$ radicals wherein $R_2$ and $R_3$ are methyl or ethyl, and $C(CH_3)_2CON(R_4)_2$ wherein $R_4$ is ethyl, the amine is a trialkyl amine and the ratio of reactants is about one mol of phosphorodichloridite, about one mol of water and about two moles of amine.

23. A method of claim 22 wherein the alkyl radical of the trialkyl amine contains 1 to 4 carbon atoms and the reaction is conducted at about 0° C.

* * * * *